United States Patent [19]

Couture-Dorschner et al.

[11] Patent Number: 5,591,147
[45] Date of Patent: Jan. 7, 1997

[54] ABSORBENT ARTICLE HAVING AN OPPOSITELY BIASED ATTACHMENT FLAP

[75] Inventors: Laurie Couture-Dorschner, Greenville; Dede A. Hirt, Menasha; William G. Stoeger, Appleton; Rebecca L. Dilnik, Neenah, all of Wis.

[73] Assignee: Kimberly-Clark Corporation, Neenah, Wis.

[21] Appl. No.: 289,814

[22] Filed: Aug. 12, 1994

[51] Int. Cl.⁶ ..................................................... A61F 13/15
[52] U.S. Cl. .......................... 604/369; 604/385.1; 604/387
[58] Field of Search ............................. 604/385.1, 386, 604/387, 369, 392, 393, 400

[56] References Cited

U.S. PATENT DOCUMENTS

| | | | |
|---|---|---|---|
| 4,285,343 | 8/1981 | McNair . | |
| 4,386,932 | 6/1983 | Pitts | 604/383 |
| 4,496,359 | 1/1985 | Pigneul | 604/387 |
| 4,608,047 | 8/1986 | Mattingly | 604/387 |
| 4,621,000 | 11/1986 | Frick | 428/40 |
| 4,687,478 | 8/1987 | Van Tilburg | 604/387 |
| 4,701,177 | 10/1987 | Ellis et al. | 604/385 A |
| 4,701,178 | 10/1987 | Glaug et al. | 604/387 |
| 4,753,644 | 1/1988 | Cottenden et al. | 604/378 |
| 4,753,645 | 6/1988 | Johnson | 604/378 |
| 4,773,905 | 9/1988 | Molee et al. | 604/378 |
| 4,790,838 | 12/1988 | Pigneul et al. | 604/366 |
| 4,798,601 | 1/1989 | Shirose | 604/368 |
| 4,822,435 | 4/1989 | Igaue et al. | 156/164 |
| 4,834,739 | 5/1989 | Linker, III et al. | 604/385.1 |
| 4,862,574 | 9/1989 | Seidy | 29/415 |
| 4,865,597 | 9/1989 | Mason, Jr. et al. | 604/385.1 |
| 4,900,319 | 2/1990 | Richwine | 604/385.1 |
| 4,911,701 | 3/1990 | Mavinkurve | 604/385.2 |
| 4,936,839 | 6/1990 | Molee et al. | 604/378 |
| 4,940,462 | 7/1990 | Salerno | 604/387 |
| 4,950,264 | 8/1990 | Osborn, III | 604/385.1 |
| 4,963,139 | 10/1990 | Dabroski | 604/378 |
| 5,009,653 | 4/1991 | Osborn, III | 604/385.1 |
| 5,011,480 | 4/1991 | Gossens et al. | 604/385.1 |
| 5,037,418 | 8/1991 | Kons et al. | 604/387 |
| 5,087,254 | 2/1992 | Davis et al. | 604/386 |
| 5,092,860 | 3/1992 | Pigneut | 604/380 |
| 5,098,422 | 3/1992 | Davis et al. | 604/385.1 |
| 5,125,918 | 6/1992 | Seidy | 604/386 |
| 5,133,704 | 7/1992 | Wheeler | 604/387 |
| 5,133,705 | 7/1992 | Nakanishi et al. | 604/387 |
| 5,151,091 | 9/1992 | Glaug et al. | 604/385.1 |
| 5,154,715 | 10/1992 | Van Iten | 604/387 |
| 5,167,654 | 12/1992 | Yang | 604/385.2 |
| 5,171,302 | 12/1992 | Buell | 604/385.1 |
| 5,181,563 | 1/1993 | Amaral | 604/385.2 |
| 5,197,959 | 3/1993 | Buell | 604/385.1 |
| 5,201,727 | 4/1993 | Nakanishi et al. | 604/390 |
| 5,217,448 | 6/1993 | Glaug et al. | 604/397 |
| 5,219,341 | 6/1993 | Serbiak et al. | 604/361 |
| 5,221,275 | 6/1993 | Van Iten | 604/387 |
| 5,234,422 | 8/1993 | Sneller et al. | 604/385.2 |
| 5,308,346 | 5/1994 | Sneller et al. | 604/385.2 |
| 5,344,416 | 9/1994 | Niihara | 604/385.1 |
| 5,346,486 | 9/1994 | Osborn, III et al. | 604/385.1 |

FOREIGN PATENT DOCUMENTS

| | | | |
|---|---|---|---|
| 0426235A3 | 5/1991 | European Pat. Off. . | |
| 0530781 | 3/1993 | European Pat. Off. | 604/386 |
| 2244653 | 12/1991 | United Kingdom | 604/387 |

*Primary Examiner*—Mary Beth Jones
*Attorney, Agent, or Firm*—Mark L. Davis

[57] ABSTRACT

An absorbent article having at least one flap for attachment to the undergarment of a wearer is disclosed. The absorbent article includes biasing means for disposing the flap in an outward direction relative to the undergarment facing side of the absorbent article.

20 Claims, 3 Drawing Sheets

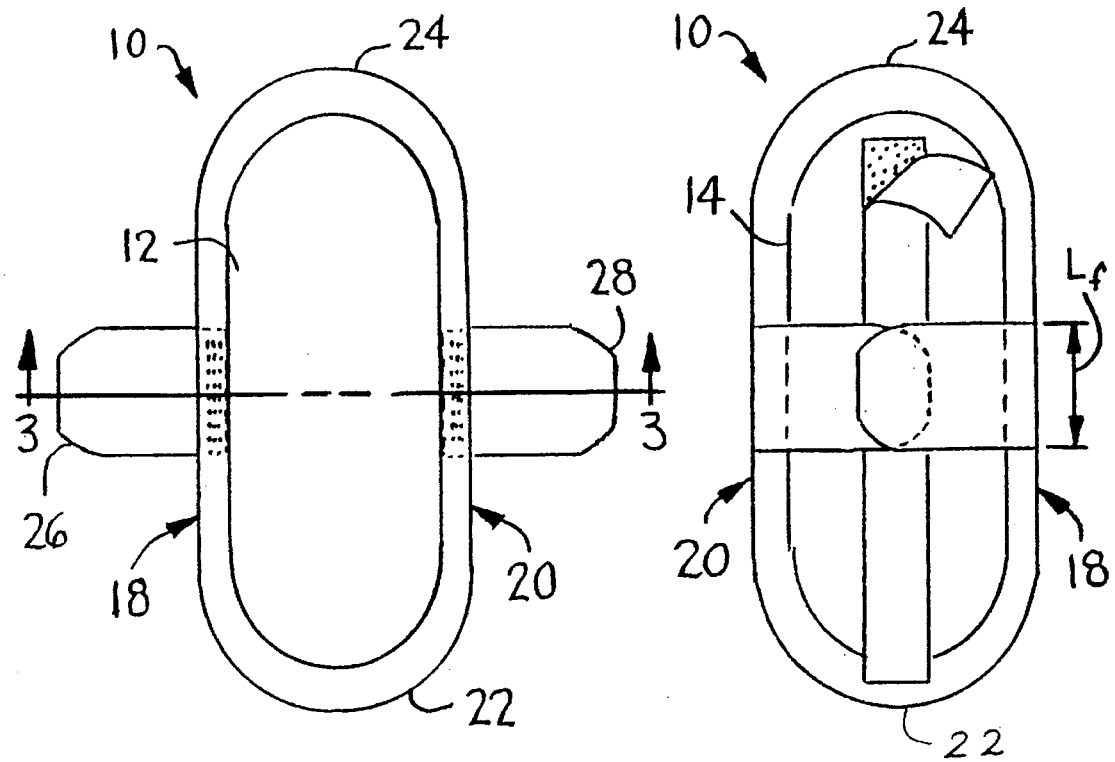
FIG. 1
FIG. 2
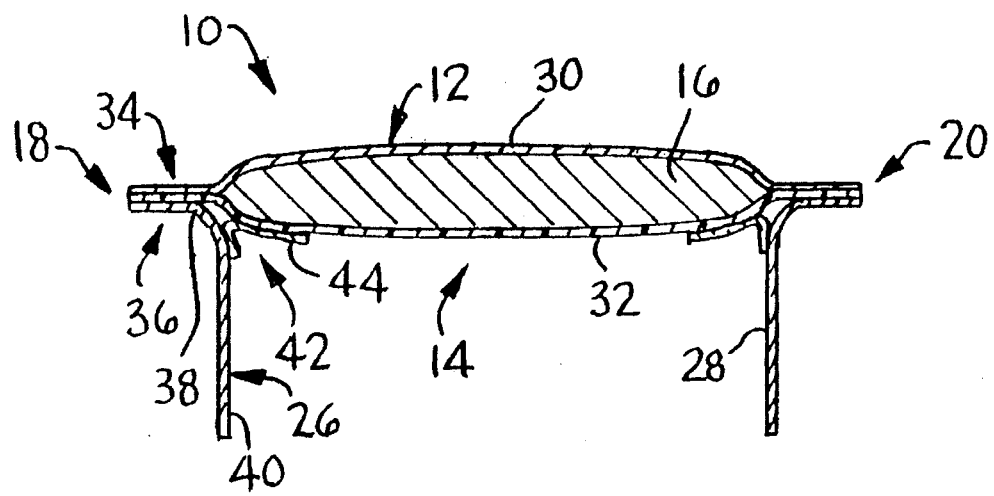
FIG. 3

ABSORBENT ARTICLE HAVING AN OPPOSITELY BIASED ATTACHMENT FLAP

BACKGROUND OF THE INVENTION

This invention relates to an absorbent article having attachment means extending transversely, relative to the absorbent, for securing the absorbent article during use. More particularly, this invention relates to an absorbent article having at least one attachment panel, flap or wing that is biased in an outward direction relative to the position normally assumed by the panel, flap or wing during use.

Unitary disposable absorbent articles generally all have the same basic structure. An absorbent core that is encased between a liquid-pervious cover, and a liquid-impervious baffle. Numerous variations of the elements in addition to the basic cover, baffle and absorbent core arrangement are known. Each additional element is usually directed to improving a specific characteristic of the absorbent article. Such absorbent articles are now in a wide use as sanitary napkins, panty shields, panty liners and adult incontinence pads. While this invention is directed to all such products, for purposes of simplification, these products will be referred to collectively herein simply as sanitary napkins. Generally, such prior products have performed well, remaining in place and providing the user with ease of placement and removal. However, these products have suffered from certain drawbacks. For example, the inner crotch surface of an undergarment, to which these products are typically adhered, is continually being distorted, twisted and stretched due to the dynamics of the wearer. As a result, frequently the adhesive attachment detaches with the undesirable consequence of the napkin moving out of place. Further, while a napkin frequently reattaches due to the continuing adhesive nature of the pressure sensitive adhesive, reattachment often places the napkin in an undesirable position wherein the napkin does not function properly. In an extreme case, the attachment of the adhesive also results in the adhesive folding over on itself and then becoming unavailable for reattachment.

In an effort to overcome the loss of protection due to the lack of close contact with the body of the wearer, and to ameliorate the above problem, the disposable absorbent article art has been introduced to products having side panels, flaps or wings that generally extend transversely, relative to the longitudinal sides of the central absorbent. As used herein "panels, flaps or wings" will hereinafter be collectively referred to as a flap or flaps. The flaps, which are intended to be folded around the edges of the crotch region of the wearer's panty, are either integral with the cover and/or baffle or fashioned from separate pieces of material attached to the sanitary napkin. When the flaps are separate pieces of material, they have been attached either at the longitudinal edge of the sanitary napkin, or inward thereof. Although the flaps have greatly assisted in properly orienting the sanitary napkin in the crotch of the user's undergarment and in protecting the undergarment from side failures of the sanitary napkin, the flaps have been problematic in their initial placement into the crotch area of the undergarment. Typically, when the protective adhesive peel strip is removed from the garment side of the sanitary napkin, exposing the garment adhesive, the flaps, undesirably, fold inward contacting this adhesive. Thus, the flaps can become adhered to the garment side of the baffle. The user then must extricate the flap prior to placing the sanitary napkin in the crotch portion of the undergarment. It is possible the flap also includes a garment adhesive for added securement. Accordingly, the inadvertent adhering of the flap to the baffle can result in the pad becoming unusable.

Therefore, a need exists for a sanitary napkin having panty protecting flaps which can be secured to and removed from the panty more conveniently and that are easier to use.

SUMMARY OF THE INVENTION

Briefly, the present invention relates to an absorbent article having a pair of longitudinal sides, a body-facing surface, an oppositely disposed undergarment-facing surface, at least one flap adjacent to one of the longitudinal sides and a biasing device adjacent to the flap for disposing the flap in an outward direction relative to the longitudinal side. The biasing device functions to hold the flap directionally outward from the longitudinal side of the sanitary napkin, i.e., outwardly from position normally assumed by the flap during use, but still allows the flap to be positioned for use. Advantageously, the biasing device reduces, and in some cases, eliminates the likelihood of the flap attaching to undergarment-facing surface of the absorbent article prior to the absorbent article being placed in the undergarment for use.

It is a general object of this invention to provide an absorbent article having at least one flap that is easier to place for use. A more specific object of this invention is to provide an absorbent article having at least one flap that is oppositely biased relative to the position normally assumed by the flap during use.

It is another object of the invention to provide a sanitary napkin having flexible flaps that is easier to place in the crotch area of a user's undergarment.

Another object of the invention is to provide a sanitary napkin having flaps with a biasing device for holding the flap(s) outward relative to the longitudinal sides of the sanitary napkin.

Other objects and advantages of the present invention will become apparent to those skilled in the art in view of the following description and the accompanied drawings.

BRIEF DESCRIPTION OF THE DRAWINGS

FIG. 1 is a body-side plan view of a sanitary napkin according to the invention illustrating flaps spread open as the flaps may be before placement of the sanitary napkin into the crotch portion of the user's undergarment.

FIG. 2 is an undergarment or bottom plan view of a sanitary napkin showing the flaps in a closed or in use position.

FIG. 3 is a cross-sectional view of FIG. 1 taken along line 3—3 illustrating how the biasing device positions the flaps outward relative to the position normally assumed by the flaps during use and away from the undergarment-facing surface.

DETAILED DESCRIPTION OF THE PREFERRED EMBODIMENTS

Figure 4:
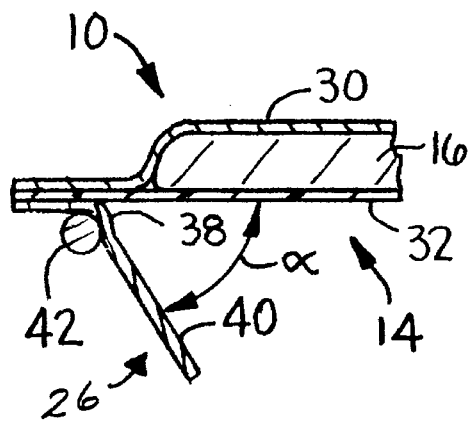
FIG. 4 is a cross-sectional view of an alternative embodiment of the invention illustrating the biasing device positioned adjacent to the longitudinal side of the sanitary napkin and the flap.

With reference to the drawings, and particularly to FIGS. 1–3 thereof, an absorbent article 10, such as a panty liner, incontinent garment, urinary shield or sanitary napkin is shown. For the purposes of description only, the absorbent article 10 will be described herein as a feminine pad or sanitary napkin. Accordingly, the sanitary napkin 10 is depicted as having a body-facing surface 12, an undergarment-facing surface 14 and an absorbent 16 positioned therebetween. The sanitary napkin 10 also has a pair of longitudinally extending sides 18 and 20, transverse ends 22 and 24 and a pair of transversely extending flaps 26 and 28.

Typically, the body-facing surface 12 includes a liquid-permeable cover 30. The cover 30, which is designed to contact the wearer's body, can be made from a film, and from woven or nonwoven fibers or strands produced from natural or synthetic materials which are easily penetrated by body fluids. Thermoplastic polymer films made from polyethylene or polypropylene are preferred. Other acceptible covers might be produced by laminating film and fiber substrates. It can also be beneficial to aperture or emboss (not shown) the cover 30 to increase the rate at which the body fluids can penetrate down and into the absorbent 16.

The undergarment-facing surface 14 can include a baffle 32 which is designed to permit the passage of air and moisture vapor to the outer surface while blocking the passage of liquids. The baffle 32 can be made from a polymeric film such as polyethylene, polypropylene, cellophane, a bicomponent film or a film/nonwoven laminate and the like. The baffle 32 can also be constructed from a liquid-permeable material that has been treated or coated to become liquid-impervious.

The absorbent 16 may be comprised of any of the well known absorbent materials used indisposable absorbent products for absorbing body fluid. For example, absorbent materials such as cellulose fibers, wood pulp, regenerated cellulose or cotton fibers. Such fibers may be chemically or physically modified. The absorbent 16 may include any of the above fibers in combination with other materials, both natural and synthetic, such as hydrophilic foams, hydrophilic polymers or the like. Wood pulp is frequently the material of choice primarily because it is inexpensive and readily available. The absorbent 16 may also include a thin absorbent layer of material such as tissue, fabric or the like made of cellulosic fibers.

As is shown in FIG. 3, the cover 30 and baffle 32 extend beyond the absorbent 16 and are bonded or joined together to form the longitudinal side edges 18 and 20. It should be noted that alternatively, the cover 30 can be wrapped entirely about the absorbent 16 and then the baffle 32 can be attached to the lower surface of the cover 30 by end seals, not shown.

The sanitary napkin 10 generally has an overall length of between about 10 to about 30 centimeters (cm) and a width of between about 2 to about 9 cm. The thickness of the sanitary napkin 10 can vary from a couple of millimeters (mm) to about 20 millimeters.

The sanitary napkin 10 includes at least one flap 26 extending transversely from at least one of the longitudinal sides 18 or 20. In the preferred embodiments illustrated in FIGS. 1–10, each of the longitudinal sides 18 and 20 includes a flap 26 or 28, respectively. The flaps 26 and 28 which are depicted as facing inward are attached to the longitudinal sides 18 and 20. The flaps 26 and 28 can also be positioned in an outward position relative to the longitudinal sides 18 and 20. Since each of the flaps is similar, only one hereinafter will be described. However, it is to be understood that the description applies equally to additional flaps if so included. Referring to FIG. 2, the flap 26 consists generally of a rectangular sheet of material having a predetermined length $L_f$ as measured along the longitudinal side 18 and is depicted as extending inward toward the absorbent 16. Referring to FIG. 3, the longitudinal side 18 has an upper portion 34 and a lower portion 36 formed by the respective extensions of the cover 30 and the baffle 32. In assembly, the flap 26 has a fixed or attached portion 38. The fixed portion 38 is adjacent to the longitudinal side 18 and is secured to the lower portion 36. The flap 26 has an edge that is coterminous with the longitudinal side 18 but it can also be located inward from the longitudinal side 18. Immediately adjacent to the fixed portion 38 is a free portion 40. The free portion 40 is the remaining portion of the flap 26. The free portion 40 is that portion of the flap 26 that is allowed to diverge and extend away from the undergarment-facing surface 14. The general construction of the sanitary napkin 10 and the flaps 26 and 28 is further described in the commonly assigned and co-pending U.S. patent application having Ser. No. 07/954,524 filed on Sep. 30, 1992, entitled "Sanitary Napkin With Garment Attachment Panels" the entire disclosure of which is incorporated herein and made a part hereof.

The sanitary napkin 10 has a biasing device 42 for disposing the flap 26 in an outward direction positioned adjacent to the flap 26. The biasing device can include any three dimensional material and preferably the material is resilient and/or elastomeric. As used herein the term "three dimensional" means that the biasing device 42 has a measurable length, width and height dimension greater than about 0.10 millimeters, preferably greater than 0.25 millimeters and more preferably greater than 0.5 millimeters. In the context of this invention, "resilient" refers to the ability of a material to return or spring back to approximately its original position i.e. returning to at least 60% its original dimension, after having been bent in an angle of 90 degrees or less, compressed to a thickness of 50% of its original thickness or both. Materials suitable for use as a biasing device 42 can be multiple layers of material that individually would not be 3 dimensional, as defined herein, but collectively meet this criteria. For example, the biasing device can be constructed of materials used in manufacturing the sanitary napkin 10. The biasing device 42 can also include having the material used in constructing the flap 28 folded, rolled or layered and affixed to the sanitary napkin 10 so that the flap 26 is disposed outwardly.

Other suitable materials include resilient materials that have a crush resistance ranging from about 5 grams to about 75 grams and desirably from about 15 grams to about 50 grams. Crush resistance may be measured by an ASTM Circular Bend Flex Test, as described in ASTM publication D 4032-82, the entire disclosure of which is incorporated herein and made a part hereof. For the purpose of this invention, the plunger described in ASTM D 4032-82 has been modified to have a smaller diameter of 6.25 millimeters, an end tip radius of 2.97 millimeters and a needle point extending 0.88 millimeters from the end of the tip. The needle has a 0.33 millimeters base diameter and a point having a radius of less than 0.5 millimeters.

A useful class of resilient materials for this invention is flexible foams such as cellular plastics. A flexible foam which is most preferred for this invention is one that does not rupture when a 20×2.5×2.5 cm piece is wrapped around a 2.5 cm mandrel at a uniform rate of 1 lap/5 seconds at 15°–25° C. Desirably, the foams are polyolefinic foams made from base polymers of polyethylene and polypropylene. Other suitable foams for use in this invention include polyurethane, cellular polystyrene, cellulose acetate, poly(vinyl chloride), silicone and latex.

Referring again to FIG. 3, the biasing device 42 includes a member 44. Desirably, the member 44 is constructed of a resilient material such as a closed-cell, polyethylene foam. The member 44 is affixed to the baffle 32 and to the flap 26 so that the flap 26 extends outward and away from the undergarment-facing surface 14, to an angle greater than about 20 degrees. Desirably, the member 44 is attached to the baffle 32 and to at least about 3 percent of the flap surface area that is available for attachment. The available flap surface area as used herein is the surface area of the flap corresponding to the free portion 40 of the flap 26 that is adjacent to the biasing device 42. Desirably, the member 44 is affixed to greater than about 50 percent of the available flap surface area and more desirably, the member 44 is affixed to greater than 80 percent of the available flap surface area.

Optionally, the free portion 40 of the flap 26, the biasing device 42 and/or the undergarment-facing surface 14, alone or in combination, can include a skid-resistant coating, not shown. This coating may be utilized, in combination with the flap 26, either as the only garment placement system or in combination with a conventional garment attachment adhesive. For instance, a small area of garment attachment adhesive could be used in order to hold the sanitary napkin 10 in place while the undergarment was being raised or lowered, but with the flap 26 and skid-resistant coating serving as the primary positioning device for the sanitary napkin 10 while it is being worn.

The materials suitable for the coating may be any latex or hot melt that has sufficient skid-resistant properties to hold a feminine or incontinence pad in place in an undergarment during use. The coating should present a generally smooth, pore-free and non-porous surface after application to the pad. The coefficient of friction of the coating material can be measured by a Davis Modified form of ASTM test No. D-1894-93. The D-1894 test calls for a sled wrapped with sponge rubber to be pulled across the test sample at 0.5 inches (12.2 mm) per minute. The modified Davis test involves wrapping the sled with test samples and pulling them across a Naugahyde sheet at 0.5 inches per minute. Using this test a coefficient of friction of greater than 1 has been found satisfactory. A preferred coefficient of friction is between 1 and 2.5.

The anti-skid coatings may be any suitable composition which generally fall into the following groups of materials:

Ethylene vinyl acetate copolymers applied as a hot melt or as a water based coating. The best candidates have at least 28 percent vinyl acetate.

Polyvinyl acetate normally used in water based emulsions.

Styrene-butadiene applied as an emulsion or as a hot melt.

Cellulose acetate butyrate as a hot melt.

Ethyl cellulose normally blended with a plasticizer and a resin and applied as a hot melt.

Acrylics applied as an emulsion.

Synthetic rubber hot melt such as KRATON block copolymers having elastomeric and styrenic blocks, rubber, resin, plasticizer blends.

Other hot melts such as polyethylenes (alone or blended) polyamides, etc. Typical of such compositions are the ethylene-vinyl acetate copolymers, acrylic terpolymers of methacrylic acids, acrylic copolymers, ethylene vinyl acetate/resin latex emulsions, ethylene-vinyl acetate hot melt adhesives, synthetic rubber (block copolymers with elastomeric and styrenic components) hot melt adhesives, and polyvinylacetate/resin emulsions. Such materials are available from H. B. Fuller Company, E. I. DuPont and Findley Adhesives, among others. Compositions of these types have found use as hot melt and water based coatings for barrier coating for nonwovens and/or papers.

Referring to FIG. 4 another embodiment is illustrated wherein the biasing device 42 is a three-dimensional, resilient and/or elastomeric material. Elastomeric materials are described in greater detail below. The biasing device 42 can be affixed adjacent to the undergarment-facing surface 14 so that the free portion 40 diverges from the undergarment-facing surface 14 at an angle ranging from about 20 degrees to about 180 degrees. The biasing device 42 can have a length dimension that ranges from approximately 25% to about 100 percent of the length $L_f$ of the flap 26, as seen in FIG. 2. The biasing device 42 can have a thickness ranging from about 0.25 millimeters to about 10 millimeters and an appropriate width dimension so that the biasing device 42 covers from about 3 to about 80 percent and preferably from about 15 to about 50 percent, of the available surface area adjacent to the biasing device 42.

It is important in this embodiment that the biasing device 42 be affixed to both the fixed portion 38 and the free portion 40. If the biasing device 42 is not affixed as described, then the flap 26 will not be disposed in an outwardly direction away from the baffle 32 and permitting the flap 26 to fold inward uninhibited. This could result in the flap 26 becoming adhered to a garment adhesive, if so used, thereby preventing the outward movement of the flap 26 away from the baffle 32 for placement in the user's undergarment.

Figure 5:
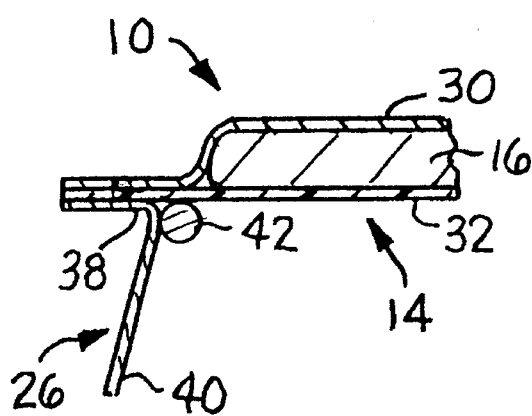
FIG. 5 is a cross-sectional view of an alternative embodiment of the invention illustrating the biasing device positioned adjacent to the undergarment-facing surface of the sanitary napkin and the flap.
Figure 6:
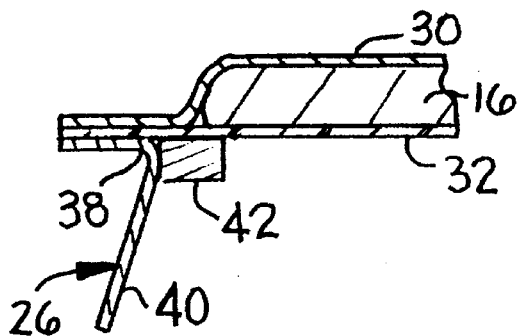
FIG. 6 is a cross-sectional view of an alternative embodiment of the invention.

Referring to FIGS. 5 and 6, the biasing device 42 which, in addition to being affixed as described in FIG. 4 above, alternatively, can be affixed solely to the baffle 32. The biasing device 42 although depicted as round and rectangular may be any 3 dimensional geometric configuration. When the biasing device 42 is affixed only to the baffle 32, the biasing device 42 can have an affixation point spaced up to about 5 millimeters from the fixed portion 38 of the flap 26. Desirably, the biasing device 42 is spaced from the fixed portion 38 a distance ranging from about 0.25 millimeters to about 3 millimeters. The biasing device 42 preferably has a thickness ranging from about 0.25 millimeters to about 10 millimeters.

Figure 7:
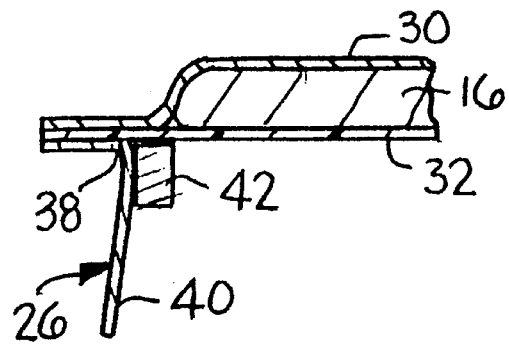
FIG. 7 is a cross-sectional view of an alternative embodiment of the invention.

Referring to FIG. 7, the biasing device 42 is positioned only on the free portion 40 of the flap 26 so that the biasing device 42 is positioned adjacent to the fixed portion 38 of the flap 26. The biasing device can have an affixation point that is spaced less than about 5 millimeters from the fixed portion 38 and preferably, it is spaced a distance ranging from about 0.25 millimeters to about 3 millimeters. The biasing device 42 preferably has a thickness ranging from about 0.25 millimeters to about 10 millimeters.

Figure 8:
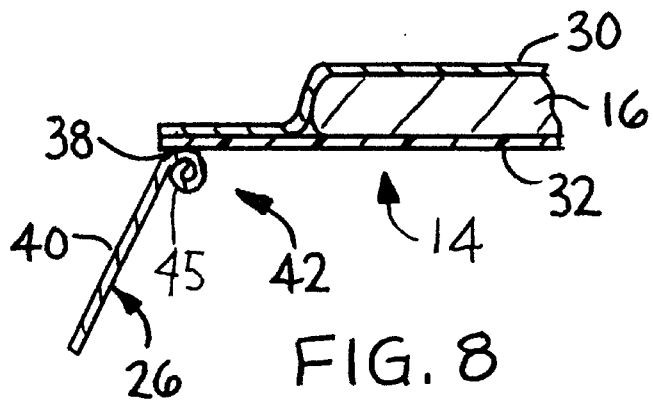
FIG. 8 is a cross-sectional view of an alternative embodiment of the invention.

Referring to FIG. 8, another embodiment of this invention is shown wherein the biasing device 42 is formed by rolling or curling one end of the flap 26 to form a loop 45. The loop 45 is then secured to itself and the baffle 32 by methods well known in the art, such as, using known construction adhesives, sonic bonding, heat sealing and the like. The loop 45 should be of sufficient diameter to bias the flap 26 away from the undergarment facing surface 14. Generally, the loop 45 will have a diameter of about 3 millimeters to about 10 millimeters and preferably from about 3 millimeters to about 7 millimeters.

Figure 9:
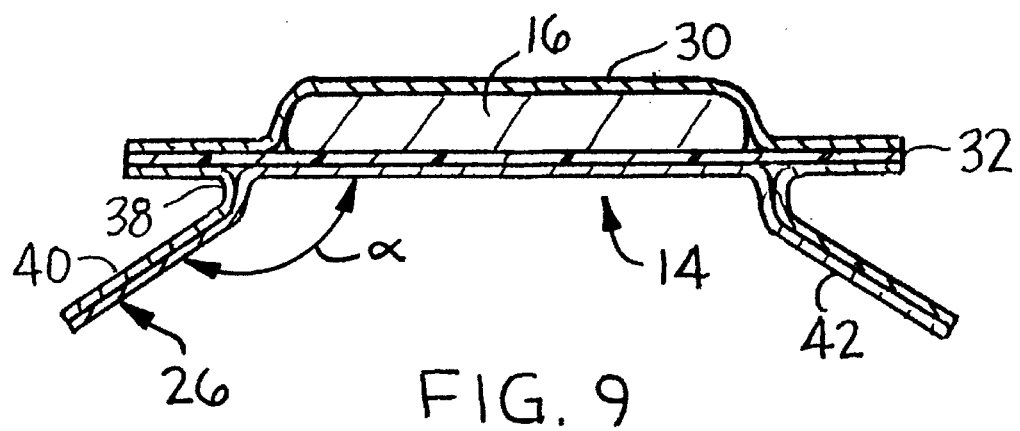
FIG. 9 is a cross-sectional view of an alternative embodiment of the invention.

Referring to FIG. 9, another embodiment of this invention is shown wherein the biasing device 42 is a polyolefinic closed cell foam that is affixed to flap 26 and extends transversely across the absorbent 16 of the sanitary napkin 10 and is affixed to the second flap 28. Preferably, the foam is a polyethylene foam. The biasing device 42 is similar to that described in FIGS. 6 and 7 above, in that it has a thickness ranging from about 0.25 millimeters to about 10 millimeters. The biasing device 42 can be affixed to the flaps 26 and 28 so that greater than about 20% of the available surface area of each flap 26 and 28 adjacent to the biasing device 42, is covered by the foam. The biasing device 42 disposes the free portion 40 of each flap away from the undergarment-facing surface 14 so that each flap forms an angle, relative to the baffle 32, ranging from about 20° to about 180°.

Figure 10:
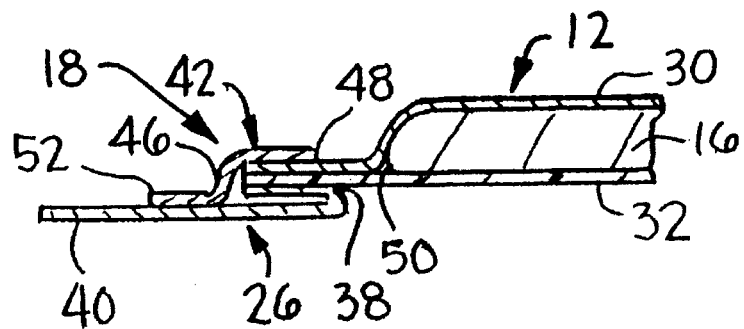
FIG. 10 is a cross-sectional view of an alternative embodiment of the invention showing the biasing device positioned on the body-facing surface of the sanitary napkin.

Referring to FIG. 10, another embodiment of the present invention is shown wherein the biasing device 42 is secured to the body-facing surface 12 and to the flap 26. Desirably, the biasing device 42 includes an elastic member 46 operatively associated with the flap 26 to provide an elastically extendable feature in the transverse direction. As used herein, the term "transverse" or "transversely" means in a direction that is perpendicular to the longitudinal edge 18 of the sanitary napkin 10. When in use, the elastic member 46 imparts an overall curvature to the sanitary napkin 10, and especially the absorbent 16 by pulling the side 18 downward and inward relative to the original position of the flap 26. This enhances the fit and comfort of the sanitary napkin 10. The elastic member 46 extends over the longitudinal side 18 of the sanitary napkin 10 and attaches to the free portion 40 of the flap 26. The elastic member 46 can be operatively associated with the flap 26 in an elastically contractible condition, so that in a normally unrestrained configuration, the elastic member 46 effectively contracts and positions the free portion 40 of the flap 26 outwardly from the longitudinal side 18. Desirably, the elastic member 46 disposes the free portion 40 outwardly to form an angle ranging from about 20 degrees to less than about 270 degrees, as measured between the baffle 32 and the free portion 40 of the flap 26.

The elastic member 46 can be secured to the flap 26 in an elastically contractible condition in a number of ways. For example, the elastic member 46 may be stretched and secured to the flap 26 while the flap 26 is in an uncontracted condition. Alternatively, the flap 26 may be contracted, for example by pleating, and the elastic member 46 can be secured to the contractive flap 26 while the elastic member 46 is in its unstretched condition. Further, the elastic member 46 may comprise heat shrinkable elastic films secured to the flap 26 in an uncontracted condition and then heated so as to cause the elastic member 46 to contract.

The elastic member 46 may be stretched to any length suitable to dispose the flap 26 into the above-described angular position without generating excessive forces that could affect the wearer's skin or adversely affect the shape of the sanitary napkin. Typically, the elastic member 46 may be stretched from about 5% to about 100%, and preferably from about 10% to about 25%.

The elastic member 46 has a first end 48 secured to the body-facing surface 12 and inward from the longitudinal side 18. Preferably, the first end 48 is secured to the cover 30 adjacent a longitudinal edge 50 of the absorbent 16. A second end 52 of the elastic member 46 is attached to the free portion 40 of the flap 26. The elastic member 46 may have any length and width dimension which disposes the flap 26 outward relative to the undergarment-facing surface. Desirably, the elastic member 46 has a length equal to the length $L_f$ of the flap 26, preferably about 50%, and most preferably about 35%. As used herein, the term "elastic" refers to a member that can increase in at least one of their dimensions in the X—Y plane. The X—Y plane is a plane generally parallel to the base of the sanitary napkin 10. When stretching forces are applied to the elastic member 46, some resistance to the stretching will result. When the stretching forces are removed, the main body portion will return to its substantially unextended or unstretched dimensions and preferably will have less than about 10% distortion in size or shape in the stretched direction.

Although the elastic member 46 can comprise a single layer of elastic material such as an elastomeric nonwoven material, preferred elastic members for the present invention comprise an elastomeric laminate comprising an elastomeric layer and a cover layer (not shown). An elastomeric laminate provides a soft comfortable surface which is non-irritating to the wearer's skin so as to provide a relatively soft longitudinal edge 18 for the sanitary napkin 10.

The elastomeric member 46 may comprise a number of different elastic materials. For example, the elastomeric member 46 may be comprised of elastomeric film (including heat shrinkable elastomeric film), "live" elastics of synthetics or natural rubber including films or strands of such elastic material, elastomeric foams, e.g. synthetic or natural rubber foams, elastomeric woven or nonwoven webs, elastomeric adhesive, or other elastomeric materials as are known in the art.

The elastic member 46 can be secured to the cover 30 using any elastic attachment means, not shown. For example, the elastic member 46 may be attached by using adhesives, stitching, ultrasonic bonding and the like. A suitable adhesive is manufactured by Findley Adhesives, Inc., of Wauwatosa, Wis., under the designation "Findley H2031".

Figure 11:
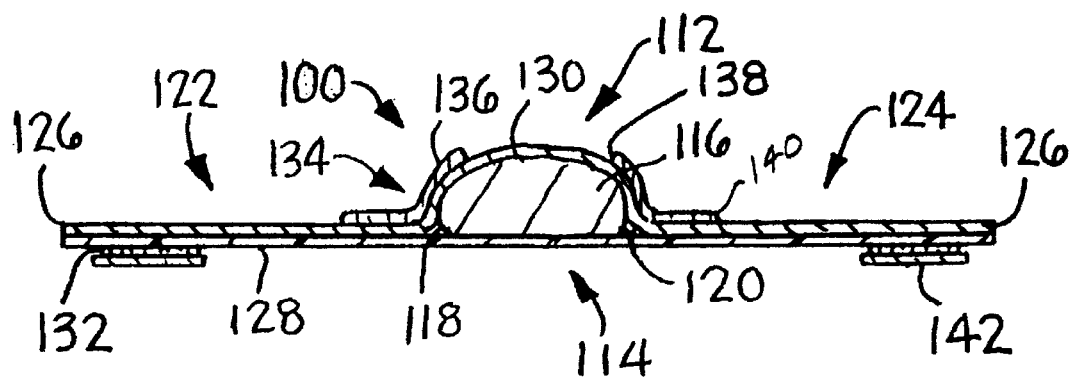
FIG. 11 is a cross-sectional view of an alternative embodiment of the invention.

Referring to FIG. 11, another embodiment of a sanitary napkin 100 is shown having a body-facing surface 112, an undergarment-facing surface 114 and an absorbent 116. The absorbent 116 has a first longitudinal side edge 118 and a second longitudinal side 120. The sanitary napkin 100 also includes a first flap 122 and a second flap 124. The flaps are that portion of the sanitary napkin 100 between the longitudinal side edge 118 or 120 of the absorbent 116 and a periphery 126 of the sanitary napkin 100. In a preferred embodiment, the flaps 122 and 124 are formed by extending a baffle 128 and a cover 130 beyond the absorbent 116 and joining the two together. The baffle 128 and cover 130 can be joined by methods well known in the art such as heat sealing or adhesively sealing around the edges of the flaps 122 and 124.

Secured to the cover 130 and the flap 122 is a transversely disposed biasing device 134 for at least partially configuring the flap 122 to be disposed in an outward direction relative to the longitudinal side edge 118 of the absorbent 116. Preferably, the biasing device 134 includes an elastic member 136 which can be secured to the longitudinal side 118 and to the flap 122.

The elastic member 136 is secured to the body-facing surface 112 and has a first end 138 adjacent to the longitudinal side edge 118. A second end 140 of the elastic member 136 is attached to the flap 122. Preferably, the second end 140 is attached to the flap 122 so that the flap 122 extends outwardly and away from the undergarment-facing surface 114 so that an angle ranging from about 20 degrees to less than about 270 degrees is formed. The angle is measured relative to the baffle 128 and the flap 122. The elastic member 136 is similar in construction and dimension to the elastic member 46 described above.

Also included with this invention are attachment elements 132 which can be made of any known pressure-sensitive adhesive material or other commonly used materials such as hook and loop type fasteners. As used herein, the term "pressure-sensitive" refers to any releasable adhesive or releasable tenacious means. Adhesive composition suitable for sanitary napkins include, for example, water-based, pressure-sensitive adhesives, such as acrylate. Alternatively, the adhesive may comprise rapid setting thermoplastic "hot melt" rubber adhesives or two-sided adhesive tape. As is customary in the art, a coated release strip 142 can be applied to protect any of the adhesive elements prior to use.

EXAMPLE 1

A sanitary napkin having flaps was constructed according to U.S. patent application having Ser. No. 07/954,524 filed on Sep. 30, 1992. Affixed to each flap was a polyethylene close-celled foam having a thickness of approximately 0.79 millimeters (mm), a length of approximately 30 millimeters and a width of approximately 20 millimeters. An example of a foam used in this embodiment may be purchased from Sealed Air Corporation, 7110 Sante Fe Drive, Hodgkins, Ill. 60525 U.S.A. The grade specification is: Cell-Aire® Foam, CA-30, thickness of 1/32 inch, density of 1.2 pounds per cubic foot, width of 60 inches, on rolls having a linear length of 2000 feet. Another foam suitable for use in the invention is available from Ametek Microfoam Division, Brandwine Four Building, Routes 1 and 202, Chadds Ford, Pa. 19317 U.S.A., called microfilm®.

The resilient member was affixed to the flap by a hot melt adhesive of the type well known in the art. Each flap was folded over and mutually affixed by contacting each flap to the other. The flaps were allowed to remain in this position for 10 minutes. The flaps were then detached. Supporting the napkin by the transverse ends and with the body-facing surface upward, each flap was disposed outwardly at an angular relationship, relative to the baffle, by about 120°.

EXAMPLE 2

The sanitary napkin of Example 1 was made with the following modification. Instead of having a polyethylene close-celled foam, an elastic member was attached to the cover and each flap. The elastic member was attached at the longitudinal edge of the absorbent and to the free portion of each flap. The elastic member was approximately 20 mm in length, 17 mm in width and attached approximately 17 mm onto the free portion of the flap. The flaps were folded over and allowed to come into contact so that the flaps were secured to each other. The flaps were allowed to remain in this position for 10 minutes. The flaps were then detached. Supporting the napkin by the transverse ends and with the body-facing surface upward, each flap was disposed outwardly at an angular relationship. Relative to the baffle and the free portion of the flap, the angle was greater than 150°.

While the invention has been described in conjunction with several specific embodiments, it is to be understood that many alternatives, modifications, and variations will be apparent to those skilled in the art in light of the foregoing description. Accordingly, this invention is intended to embrace all such alternatives, modifications and variations which fall within the spirit and scope of the appended claims.

We claim:

1. An absorbent article having a pair of longitudinal sides, said absorbent article comprising:
    a) a fluid-pervious cover;
    b) a fluid-impervious baffle;
    c) an absorbent between said cover and said baffle;
    d) a flap extending inwardly from and positioned adjacent to one of said longitudinal sides, said flap having a fixed portion secured to said baffle and a free portion adjacent to said fixed portion; and
    e) biasing means for urging said free portion of said flap in an outward direction relative to said longitudinal side wherein said biasing means is positioned adjacent to said flap, said biasing means having a crush resistance from about 5 grams to about 75 grams.

2. The absorbent article of claim 1 further comprising a second inwardly extending flap adjacent to a second longitudinal side, said second flap having a second biasing means adjacent to said second flap for urging a free portion of said second flap in an outward direction relative to said second longitudinal side.

3. The absorbent article of claim 1 wherein said biasing means largest said free portion of said flap in a direction outwardly from said longitudinal side to form an angle ranging from about 20° to less than about 270° as measured between said baffle and said free portion of said flap.

4. The absorbent article of claim 1 wherein said biasing means is secured to said baffle.

5. The absorbent article of claim 1 wherein said biasing means is secured to said baffle and said flap.

6. The absorbent article of claim 1 wherein said biasing means is secured to said free portion of said flap.

7. The absorbent article of claim 1 wherein said fixed portion of said flap is secured to said baffle inward from said longitudinal side and said biasing means is secured to said baffle and said flap.

8. The absorbent article of claim 7 wherein said material is a polyolefinic foam.

9. The absorbent article of claim 7 wherein said three dimensional material has a thickness greater than about 0.25 millimeters.

10. The absorbent article of claim 1 wherein said biasing means includes a three dimensional material.

11. The absorbent article of claim 10 wherein said foam is a close-celled foam.

12. The absorbent article of claim 11 wherein said biasing means is a resilient material.

13. The absorbent article of claim 11 wherein said biasing means is an elastomeric material.

14. The absorbent article of claim 11 wherein said flap has a predetermined length and said biasing means substantially extends the length of said flap.

15. An absorbent article having a pair of longitudinal sides, transverse ends, a body-facing surface, and an undergarment-facing surface, said absorbent article comprising:

a) a fluid-pervious cover;

b) a fluid-impervious baffle;

c) an absorbent between said cover and said baffle;

d) a flap adjacent to each of said longitudinal sides, said flaps extending inwardly from said longitudinal sides, each of said flaps having a fixed portion and a free portion wherein said fixed portion is secured to said undergarment-facing surface and said free portion is adjacent to said fixed portion; and e) biasing means positioned adjacent to each flap for urging said flaps in an outward direction relative to said longitudinal side, said biasing means having a crush resistance from about 5 grams to about 75 grams.

16. The absorbent article of claim 15 wherein said biasing means includes a resilient, three dimensional polyolefinic foam affixed to said baffle and said flap.

17. The absorbent article of claim 16 wherein said foam has a thickness ranging from about 0.25 millimeters to about 10 millimeters.

18. The absorbent article of claim 15 wherein said free portion of said flap has a predetermined surface area adjacent to said biasing means and said biasing means is affixed to at least about 3 percent of said surface area.

19. The absorbent article of claim 15 wherein said biasing means is affixed to said baffle at an affixation point that is spaced from said fixed portion of said flap by a distance of less than about 5 millimeters.

20. A sanitary napkin having a pair of longitudinal sides, transverse ends, a body-facing surface, and an undergarment-facing surface, said absorbent article comprising:

a) a fluid-pervious cover;

b) a fluid-impervious baffle;

c) an absorbent element between said cover and said baffle;

d) a flap adjacent to each of said longitudinal sides;

e) garment adhesive secured to said baffle toward said undergarment-facing surface; and e) biasing means adjacent to each flap for disposing said flaps in an outward direction relative to said longitudinal side wherein said means prevents said flaps from folding inward and prematurely attaching to said garment adhesive said biasing means having a crush resistance from about 5 grams to about 75 grams.

* * * * *